United States Patent [19]

Leeper

[11] Patent Number: 4,773,768
[45] Date of Patent: Sep. 27, 1988

[54] TUBE RETAINING AND DISPOSAL CONTAINER

[76] Inventor: Charles E. Leeper, P.O. Box 30, Santa Monica, Calif. 90406

[21] Appl. No.: 127,166

[22] Filed: Dec. 1, 1987

[51] Int. Cl.[4] .............................................. B65D 33/14
[52] U.S. Cl. ......................................... 383/22; 5/503; 5/508; 604/322
[58] Field of Search .................... 383/22, 23, 24, 127; 206/570, 806; 604/322, 323, 324, 325, 326; 248/95; 5/503, 508

[56] References Cited

U.S. PATENT DOCUMENTS

| | | | |
|---|---|---|---|
| 2,459,246 | 1/1949 | Sinclair | 5/503 X |
| 2,784,423 | 3/1957 | Droeger et al. | 5/503 |
| 3,138,361 | 6/1964 | Meldrum | 248/95 |
| 3,220,434 | 11/1965 | Garth | 604/322 X |
| 3,231,901 | 2/1966 | Kennedy | 383/23 X |
| 3,345,023 | 10/1967 | Scott et al. | 5/503 X |
| 3,371,897 | 3/1968 | Serany, Jr. et al. | 604/326 X |
| 3,534,738 | 10/1970 | Huck | 248/95 X |
| 4,085,755 | 4/1978 | Burrage | 604/323 |
| 4,461,442 | 7/1984 | Keenan | 248/95 X |
| 4,695,020 | 9/1987 | Collins | 248/95 X |

*Primary Examiner*—Stephen Marcus
*Assistant Examiner*—Nova Stucker
*Attorney, Agent, or Firm*—Poms, Smith, Lande & Rose

[57] ABSTRACT

A tube retaining and disposal container comprising a mounting board insertible between the mattress and frame of a hospital bed or the like. A disposable bag, preferably sterile, is secured to the board, open at the top, and extending vertically with respect to the plane of the mattress. An aperture is provided in the board above the open end of the bag and a tube, connected at one end to a source of suction and open at the other end, can be doubled with the doubled-over portion insertible into the aperture. This stops any liquid flow out of the open end of the tube which open end can be disposed in the bag. When use of the tube is completed, the tube can be dumped in the bag, along with any gloves used by the doctor, nurse or other hospital worker, and the bag and container disposed of.

17 Claims, 1 Drawing Sheet

TUBE RETAINING AND DISPOSAL CONTAINER

BACKGROUND OF THE INVENTION

1. Field of the Invention

The invention relates to hospital devices; and, more particularly, to a disposable container for a fluid-containing suction tube or the like.

2. Description of the Prior Art

In recent years, there has been much concern with the AIDS virus and other communicable diseases that may be encountered in a hospital environment. For these reasons, hospitals have attempted to make disposable as many devices as possible that are used in patient care. These problems, particularly with regard to the AIDS virus, are especially serious where blood is involved. In at least one reported case, a hospital worker was infected with the AIDS virus through a syringe needle that accidentally stuck her when taking a blood sample from a patient even though the worker was wearing a protective gown and gloves.

In one such hospital operation, a source of suction is provided and a tube extends from this source of suction to a T-shaped catheter having a second tube portion leading therefrom and a vertical Tee section open at the top. The hospital worker uses the free end of the tube to suck out any mucus, blood, vomit, etc. from the patient. Suction is controlled by placing one's finger over the open Tee section. The hospital worker wears gloves during this procedure and folds the open end of the tube on itself and clamps the folded end at some convenient location until ready for use, such as between preexisting wires on a machine adjacent the patient's bed, under the patient's mattress, etc. This is quite inconvenient since the folded tube end may get dislodged and fall, it may leak or get contaminated, etc.

There is thus a need for a sterile environment in which to hold a suction tube until ready for use in a convenient location, then allow disposal of the tube and gloves worn by the hospital worker, along with the device used to carry out the same.

SUMMARY OF THE INVENTION

It is an object of this invention to provide a disposable tube retaining and disposal container for use with suction tubes or the like.

It is a further object of this invention to provide such a container which holds one end of a suction tube in a location near a patient, then can accommodate both the tube and gloves worn by the hospital worker for quick and easy disposal.

It is still further an object of this invention to provide such a container which is economic to manufacture, made of compact foldable parts, and can be packaged in a sterile manner.

These and other objects are accomplished by providing a tube retaining and disposal container comprising a mounting board insertible between the mattress and frame of a hospital bed or the like. A disposable bag, preferably sterile, is secured to the board, open at the top, and extending vertically with respect to the plane of the mattress. An aperture is provided in the board above the open end of the bag and a tube connected at one end to a source of suction and open at the other end can be doubled with the doubledover portion insertible into the aperture. This stops any liquid flow out of the open end of the tube which open end can be disposed in the bag. When use of the tube is completed, the tube can be dumped in the bag, along with any gloves used by the doctor, nurse or other hospital worker, and the bag and container disposed of.

DESCRIPTION OF THE PREFERRED EMBODIMENT

Figure 1:
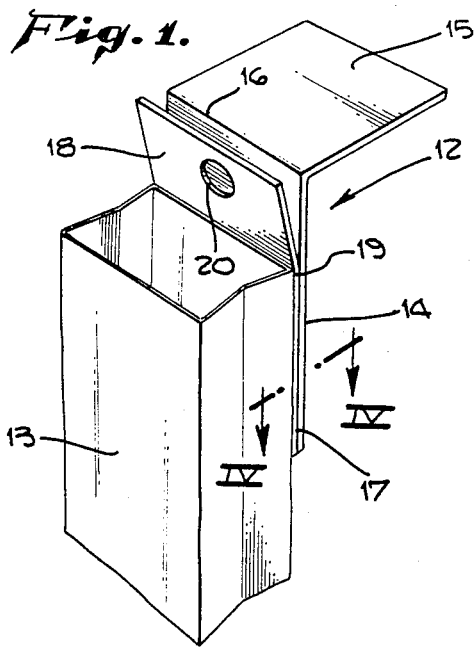
FIG. 1 is a perspective view of a tube retaining and disposal container, showing a tube connected thereto, in accordance with the teachings of the invention.

Referring now to FIG. 1 of the drawing, a tube retaining and disposal container 10 is shown. It is to be understood that a tube 11 (FIG. 3) of a conventional surgical tube of suitable material, such as rubber, may be coupled to a source of suction. Such tubes are used to suck out blood, vomit, mucus, etc. from a patient. The hospital employee using the same generally wears sterile gloves during such operations and the tube itself is sterile.

Figure 4:
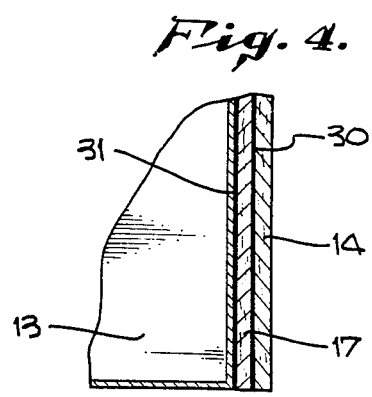
FIG. 4 is a view taken along lines IV—IV of FIG. 1.

As seen in FIG. 1, the container 10 includes a mounting board 12 and a bag 13. As particularly seen in FIG. 4, the mounting board 12 may be of parts glued or otherwise secured to each other. Thus, a first part 14 (FIGS. 1 and 4) is connected to a second part 15 forming a flap foldable along hinge line 16. A fourth part 17, secured to part 14 as by gluing 30 (FIG. 4) or the like, with a third part 18 integral with part 17, foldable along hinge line 19.

Bag 13 is a collapsible bag open at the top with the upper rear portion secured to part 17 as by gluing 31 (FIG. 4) or the like.

Figure 2:
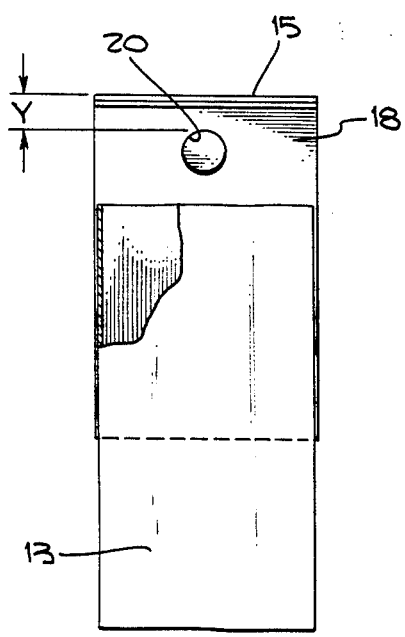
FIG. 2 is an elevational view of the tube retaining and disposal container alone of FIG. 1.
Figure 3:
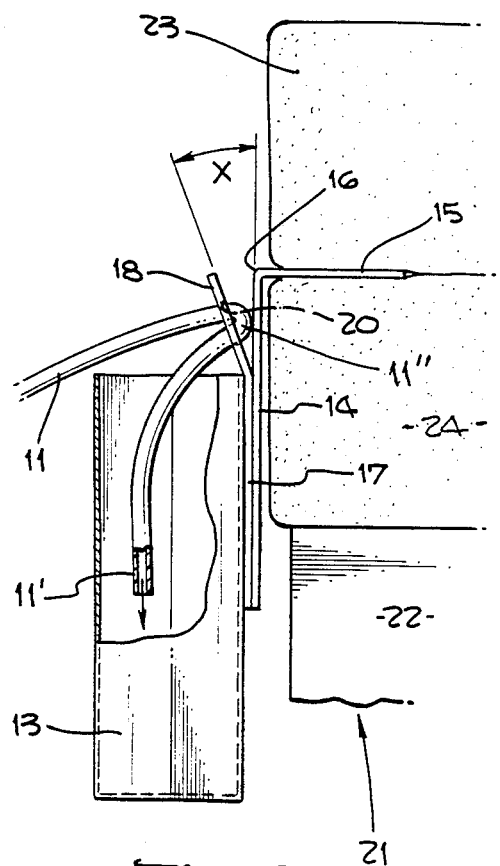
FIG. 3 is a side view of the arrangement of FIG. 1 in operative position between the mattress and frame of a bed.

As seen in FIG. 2, part 18 has an aperture 20 which may be circular and of a size at least slightly smaller in diameter than twice the diameter of tube 11. As seen in FIG. 3, the end 11' of tube 11, extends into the interior of bag 13. A short distance from end 11', tube 11 is doubled over and the doubled-over portion 11" is inserted into aperture 20 and retained therein thus holding end 11' inside bag 13.

As seen in FIG. 3, a portion of a conventional hospital bed 21 is shown having a bottom frame 22, a box spring 24 and a mattress 23 thereon. As seen, the part 15 of board 12 is inserted between mattress 23 and box spring 24 and retained therein while presenting part 18 outside of bed 21 with bag 13 hanging down. Of course, part 15 can be inserted between any bed portions, e.g., between a mattress and a bed frame.

Preferably, board 12 is made of a stiff lightweight material, such as plastic or cardboard, and provided with a smooth water-resistant surface. Board 12 may be of any suitable thickness, such as about 1.5 to 2.0 mm. thick. The container 10 may be of any suitable dimensions. For example, part 15 may be square-shaped and about 6×6 inches in area. Part 14 may be about 6" wide, where it is attached to part 15, and about 8" long. Part 17 may be about 6×6 inches with part 18 thus about 6×2 inches. The angle x (FIG. 3) may be about 30°. Of course, this angle can vary and part 18 may be either rigidly set at that angle, or flexible and foldable about hinge 19 to be moved to that angle and stay in position.

Thus, any suitable materials and dimensions may be used as long as part 18 can retain and hold in position tubing 11 as seen in FIG. 1.

Aperture 20 may be centered in part 18 and, if circular, may be about 1.3 cm. in diameter. Aperture 20 can of course take other configurations, such as oval, and, if oval, about 1" by 1.3 cm. in size. The distance y (FIG. 2) may be about 1 cm.

Bag 13 may also be about 6" wide, about 4" deep when in an open position, and about 12" long and foldable to a flat position when not in use. Preferably, bag 13 is made of a water-resistant material and be sufficiently stiff to either remain in an open position or in a folded position. For example, stiff paper, cardboard or plastic may be used.

The entire package, i.e., bag 13 and board 12, but not tube 11, may be packaged in a sterile container. After use of tube 11, the entire tube 11 can be dumped inside of bag 13 along with the gloves of the hospital worker and everything can be discarded. Thus, the entire container 10, tube 11 and gloves are disposed of and contamination is avoided.

The container is thus easy to manufacture, economical and disposable. It is simple to use and can be sterile when taken out of its wrappings and maintain the free end of tube 11 is a sterile condition. Any drippings out of the open end 11' of tube 11 drip into bag 13.

There is thus described an inexpensive device for holding tubing in a position for use, then accommodating disposal of the same. Although I have described a particular embodiment of the invention, variations thereof may occur to an artisan and the scope of the invention should be determined only by the scope of the appended claims.

I claim:

1. A disposable combination tube retaining and disposal container for insertion between the mattress and box spring of a bed comprising:
   a flexible collapsible bag 13 open at the top and closed on the sides and bottom thereof;
   a mounting board 14, 15, 18 bonded to the bag in a manner whereby the bag is disposed in a vertical position with said open top facing upwardly;
   said board 14, 15, 18 including a first vertical part 14 having said bag secured thereto, a second part 15 extending generally normal to said first part 14 in a direction away from said bag and said second part 15 being of a length sufficient for insertion between the mattress and box spring of a bed so that said second part 15 may be clamped between said bed spring and mattress and provide the sole support for said combination with respect to said bed without clamping of the same to said bed, and a third part 18 integral with said first part 14 extending at an angle with respect to said first part 14 and in a direction toward said bag and overlying the open top thereof; and
   a circumscribed aperture 20 through said third part 18 above the open top of said bag whereby a tube 11 having an open end can be folded on itself with the open end thereof disposed inside said bag with the folded tube portion inserted into said aperture and retained therein.

2. In the combination of claim 1 wherein said board includes a fourth part 17 secured to said first part 14 and parallel thereto with said third part 18 integral with said fourth part 17.

3. In the combination of claim 2 wherein said second part 15 is hingedly secured to said first part 14.

4. In the combination of claim 3 wherein the overall width of all of said parts are substantially the same.

5. In the combination of claim 4 wherein the overall length of said first and third parts 14, 18 is substantially the same as the overall length of said fourth part 17.

6. In the combination of claim 1 wherein said board is of a firm material having a water-resistant surface.

7. In the combination of claim 1 wherein the plane of said third part 18 is at an angle of about 30° with respect to the plane of said first part 14.

8. In the combination of claim 1 wherein said aperture 20 is a generally circular hole.

9. In the combination of claim 1 wherein said bag is of a foldable water-resistant material.

10. A combination tube retaining and disposal container comprising:
    a flexible collapsible bag 13 open at the top and closed on the sides and bottom thereof;
    a mounting board 14, 15, 18 secured to the bag in a manner whereby the bag is disposed in a vertical position with said open top facing upwardly;
    said board 14, 15, 18 including a first vertical part 14 having said bag secured thereto, a second part 15 extending generally normal to said first part 14 in a direction away from said bag, a third part 18 integral with said first part 14 extending at an angle with respect to said first part 14 and in a direction toward said bag and overlying the open top thereof; a fourth part 17 secured to said first part 14 and parallel thereto with said third part 18 integral with said fourth part 17; and
    an aperture 20 through said third part 18 above the open top of said bag whereby a tube having an open end can be folded on itself with the open end thereof disposed inside said bag with the folded tube portion inserted into said aperture and retained therein.

11. In the combination of claim 10 wherein said second part 15 is hingedly secured to said first part 14.

12. In the combination of claim 11 wherein the overall width of all of said parts are substantially the same.

13. In the combination of claim 12 wherein the overall length of said first and third parts 14, 18 is substantially the same as the overall length of said fourth part 17.

14. In the combination of claim 10 wherein said board is of a firm material having a water-resistant surface.

15. In the combination of claim 10 wherein the plane of said third part 18 is at an angle of about 30° with respect to the plane of said first part 14.

16. In the combination of claim 10 wherein said aperture 20 is a generally circular hole.

17. In the combination of claim 10 wherein said bag is of a foldable water-resistant material.

* * * * *